(12) United States Patent
Nishida et al.

(10) Patent No.: US 8,207,119 B2
(45) Date of Patent: Jun. 26, 2012

(54) OPHTHALMOLOGICAL COMPOSITION

(75) Inventors: Teruo Nishida, Ube (JP); Yorihisa Uetake, Nagoya (JP); Hiroaki Iwata, Kusagai (JP)

(73) Assignee: Nihon Tenganyaku Kenkyusho Co., Ltd., Nagoya-Shi (JP)

( * ) Notice: Subject to any disclaimer, the term of this patent is extended or adjusted under 35 U.S.C. 154(b) by 174 days.

(21) Appl. No.: 12/559,704

(22) Filed: Sep. 15, 2009

(65) Prior Publication Data

US 2010/0099629 A1 Apr. 22, 2010

Related U.S. Application Data

(62) Division of application No. 10/540,446, filed as application No. PCT/JP03/16514 on Dec. 24, 2003, now abandoned.

(30) Foreign Application Priority Data

Dec. 27, 2002 (JP) ................................ 2002-381131

(51) Int. Cl.
*A61K 38/00* (2006.01)
*A61K 43/00* (2006.01)
*C07K 14/705* (2006.01)

(52) U.S. Cl. ........................ 514/16.5; 514/1.1; 514/19.1

(58) Field of Classification Search .................. 514/1.1, 514/16.5, 19.1
See application file for complete search history.

(56) References Cited

U.S. PATENT DOCUMENTS

| 4,713,446 | A | * | 12/1987 | DeVore et al. ................ 530/356 |
| 5,733,870 | A | | 3/1998 | Alm |
| 5,840,514 | A | | 11/1998 | Livant |
| 5,989,850 | A | | 11/1999 | Livant |
| 6,025,150 | A | | 2/2000 | Livant |
| 6,140,068 | A | | 10/2000 | Livant |
| 6,221,846 | B1 | | 4/2001 | Livant |
| 6,331,409 | B1 | | 12/2001 | Livant |
| 2002/0068047 | A1 | | 6/2002 | Livant |

FOREIGN PATENT DOCUMENTS

| EP | 0223254 | * | 5/1987 |
| EP | 0 914 827 | | 5/1999 |
| EP | 1 142 585 | | 10/2001 |
| JP | 03291238 A | * | 12/1991 |
| JP | 10-017489 | | 1/1998 |
| JP | 2000-264847 | | 9/2000 |
| JP | 2002-53492 | | 2/2002 |
| WO | 97/49419 | | 12/1997 |
| WO | 98/22617 | | 5/1998 |
| WO | 00/41729 | | 7/2000 |
| WO | 01/91795 | | 6/2001 |

OTHER PUBLICATIONS

L. Aucoin et al., "Interactions of corneal epithelial cells and surfaces modified with cell adhesion peptide combinations," J. Biomater: Sci. Polymer Edn., vol. 13, No. 4, pp. 447-462 (2002).
Pubmed PMID: 12160303, citation index for L. Aucoin et al. J. Biomater. Sci. Polymer Edn, vol. 13, No. 4, pp. 447-462 (2002).
Livant, Donna L., et al., "The PHSRN sequence induces extracellular matrix invasion and accelerates wound healing in obese diabetic mice," The Journal of Clinical Investigation, Jun. 2000, vol. 105, No. 11, pp. 1537-1545.
Kenneth M. Yamada, "Fibronectin peptides in cell migration and wound repair," The Journal of Clinical Investigation, Jun. 2000, vol. 105, No. 11, pp. 1507-1509.
Zhao, Ming Wei, et al., "A Distinct Integrin-Mediated Phagocytic Pathway for Extracellular Matrix Remodeling by RPE Cells," Investigative Ophthalmology & Visual Science, Oct. 1999, vol. 40, No. 11, pp. 2713-2723.

* cited by examiner

*Primary Examiner* — Jon P Weber
*Assistant Examiner* — Thane Underdahl
(74) *Attorney, Agent, or Firm* — Burr & Brown

(57) ABSTRACT

An object is to find the minimum activity expression site of fibronectin, clarify the actions of this minimum unit in relation to opthalmological fields, and provide an opthalmological composition having this minimum unit as an effective component. This invention provides an opthalmological composition, in particular, a corneal disorder treatment agent containing the peptide, PHSRN (SEQ ID NO: 1) (Pro-His-Ser-Arg-Asn (SEQ ID NO: 1)), or Ac-Pro-His-Ser-Arg-Asn-$NH_2$, which is a derivative thereof, or a salt thereof that is allowable as a medical drug as an effective component. The preferred dosage form is an ophthalmic formulation.

7 Claims, 1 Drawing Sheet

Figure 1:
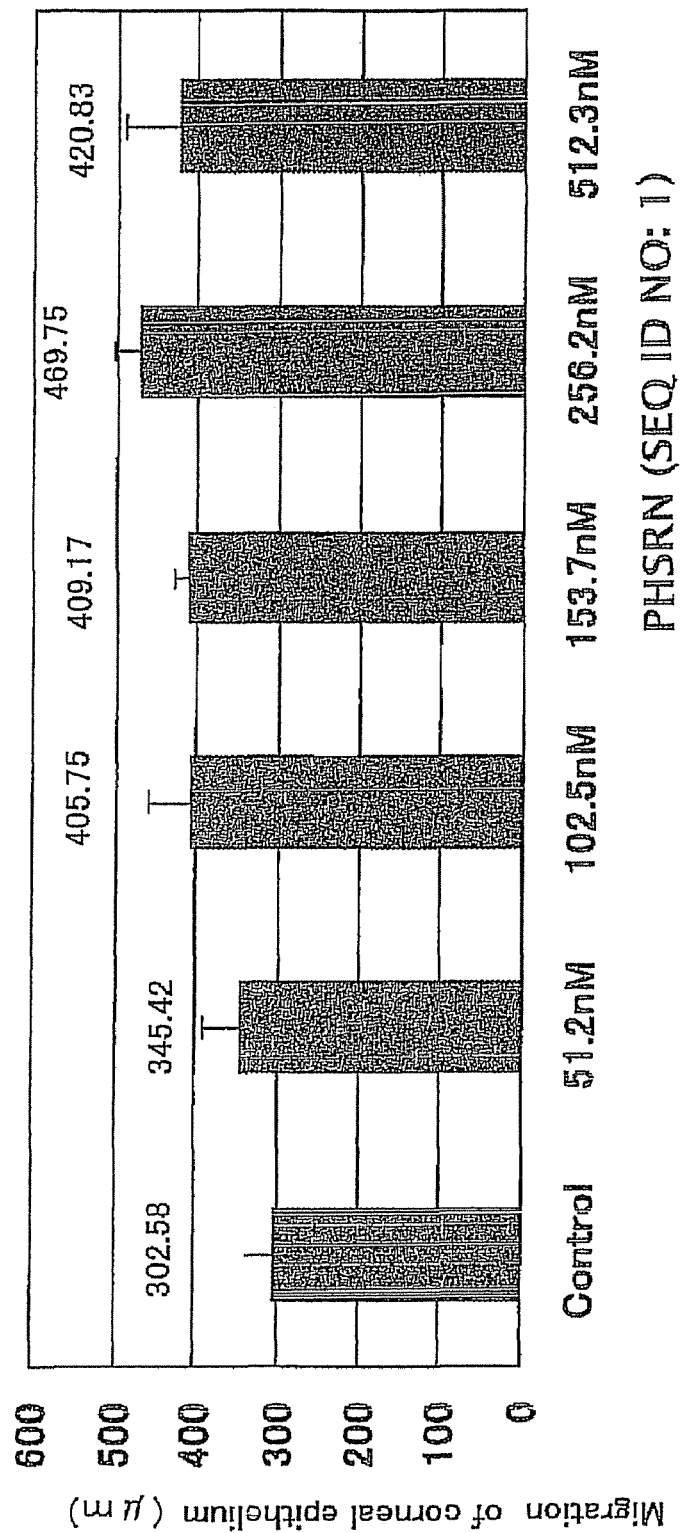

Effect of PHSRN (SEQ ID NO: 1) on the migration of corneal epithelial cells

SEQUENCE LISTING

<160> NUMBER OF SEQ ID NOS: 1

<210> SEQ ID NO 1
<211> LENGTH: 5
<212> TYPE: PRT
<213> ORGANISM: artificial
<220> FEATURE:
<223> OTHER INFORMATION: partial sequence in Fibronectin

<400> SEQUENCE: 1

Pro His Ser Arg Asn
1               5

OPHTHALMOLOGICAL COMPOSITION

CROSS REFERENCE TO RELATED APPLICATIONS

This application is a division of U.S. application Ser. No. 10/540,446, filed May 8, 2006, which is the National Phase of International Application No. PCT/JP2003/016514 having an international filing date of Dec. 24, 2003, published in Japanese on Jul. 22, 2004, and claims the benefit of Japanese Application 2002-381131, filed Dec. 27, 2002, the entirety of which is incorporated herein by reference.

FIELD OF THE INVENTION

This invention concerns an opthalmological composition.

BACKGROUND OF THE INVENTION

This invention concerns the amino acid sequence, proline-histidine-serine-arginine-asparagine (SEQ ID NO: 1), which is an activity expression site of fibronectin, and a chemical substance, with which both terminals of the above amino acid sequence are modified (these shall be referred to hereinafter as PHSRN (SEQ ID NO: 1) and Ac-Pro-His-Ser-Arg-Asn-$NH_2$). This invention also concerns either or both of an opthalmological treatment composition and a preventive composition having a salt of the above-mentioned substance that is allowable as a medical drug as an effective component thereof. This composition particularly concerns either or both of a preventive agent and a treatment agent for corneal disorder that exhibit wound healing promotion actions for corneal epithelium.

The cornea is a thin tissue of 0.52 mm to 1.0 mm thickness. The cornea is positioned at the foremost portion of the eyeball and is a highly differentiated tissue having a transmitting property and an appropriate refractive power for guiding light from the exterior to the receptors of the retina. The cornea has extremely important physiological functions. The structure of the cornea is comparatively simple. That is, the cornea has a highly ordered, microscopic, five-layer structure comprising the epithelial layer, Bowman's membrane, corneal stroma, Descemet's membrane, and endothelial cell layer.

Fibronectin is a glycoprotein with a molecular weight of approximately 440 thousand that is involved in cell adhesion and spreading and serves an important role in wound healing actions as well as in morphogenesis, development, and other biological phenomena. This fibronectin is a dimer in which two subunits of a molecular weight of 220 to 250 thousand each are bonded. Fibronectin has a domain structure. Fibronectin is involved in cell adhesion and bonds specifically with various extracellular matrices and bridges to fibronectin receptors (integrins) on cell surfaces.

Corneal disorder is induced by corneal ulcer, corneal epithelial erosion, keratitis, dry eye, and various other diseases. Such disorder is repaired naturally if there is no concurrent mixed infection. The principles of repair are: (1) the appearance of fibronectin at exposed corneal stroma portions at defective epithelial portions resulting from corneal disorder; (2) the binding of this fibronectin onto a matrix; and (3) the spreading and moving of epithelial cells onto this matrix. As the cornea is cured, fibronectin disappears from the damaged corneal portions.

Due to some reason, the repair process may be delayed or the epithelial defect may persist without being repaired. In such a case, the normal structuring of the epithelium is affected adversely and even the structures and functions of the stroma and endothelium may become impaired. Conventional treatment methods are passive methods in which the corneal surface is protected from external irritation in order to allow the epithelium to spread naturally and resurface the defective portions. With recent developments in cell biology, factors involved in the division, movement, adhesion, spreading, etc., of cells have become clarified. In regard to the repair of corneal epithelial defects, compounds that promote the spreading of the corneal epithelium have come to be emphasized.

Components, such as fibronectin, EGF (Epidermal Growth Factor), and hyaluronic acid, are known as treatment agents for corneal epithelial wounds. Fibronectin, which exists in human plasma, can be purified and used as blood product for instillation. Such an ophthalmic formulation is known to promote the resurfacing of corneal epithelial defects and the healing of epithelial wounds.

However presently, fibronectin must be purified from a patient's autologous plasma using a special purifying kit. Extreme trouble is thus taken to obtain fibronectin and a large burden is placed on the patient. Due to this reason, fibronectin is not put to adequate use even though it is clinically effective.

EGF (Epidermal Growth Factor) is a polypeptide with a molecular weight of 6000 that is known for its actions as a mitosis-promoting growth factor for corneal epithelium. It is known that when factors that inhibit the mitosis of the epithelium are present, the effects of EGF cannot be exhibited readily. In addition, in cases accompanying inflammation and in cases of diabetic keratopathy, angiogenesis occurs as a side-effect of EGF.

Hyaluronic acid is a glucosaminoglycan with a molecular weight of several million that has N-acetyl-D-glucosamine and D-glucuronic acid as constituent sugars. Hyaluronic acid is known to exhibit significant treatment effects as a treatment agent for dry eye. In regard to actions, hyaluronic acid acts on the adhesion, spreading, and movement of epithelial cells but is low in terms of epithelial cell prolification effects. Hyaluronic acid has the disadvantage of being difficult to use as an ophthalmic formulation due to increasing in viscosity at high concentration.

The peptide, PHSRN (SEQ ID NO: 1), is a pentapeptide disclosed in International Publication WO98/22617 and in "The PHSRN sequence induces extracellular matrix invasion and accelerates wound healing in obese diabetic mice," The Journal of Clinical Investigation, 105 (11), pp. 1537-1545, 2000. In these prior-art literatures, the peptide, PHSRN (SEQ ID NO: 1), is indicated as exhibiting external wound healing effects as well as invasion and prolification suppressive effects against cancer cells. However, reports that concern the peptide, PHSRN (SEQ ID NO: 1), in relation to opthalmological fields are not known.

Satisfactory corneal disorder treatment compositions are thus not known and better compositions have been desired strongly.

As mentioned above, fibronectin is recognized to be clinically effective in opthalmological fields. However, due to problems particular to blood product (for example, sanitation problems, the large burden of having to sample a patient's autologous blood, the troublesomeness of purified fibronectin from plasma, etc.), fibronectin is not used widely. In addition, since the active site of fibronectin had not been clarified adequately, there was further room for research and development towards using fibronectin as an effective component of a corneal disorder treatment agent.

This invention has been made in view of the above circumstances and an object thereof is to find the activity expression site of fibronectin and another object thereof is to provide a composition, with which the activity expression site of fibronectin can be used as either or both of an opthalmological treatment drug and a preventive drug.

SUMMARY OF THE INVENTION

In order to achieve the above objects, the present inventors focused on the peptides contained in fibronectin and examined their actions on corneal disorder. As a result, the present inventors found that PHSRN (SEQ ID NO: 1), which is the activity expression site of fibronectin, promotes the healing of corneal epithelial wounds.

That is, the present inventors (1) found a new application of PHSRN (SEQ ID NO: 1) in an opthalmological composition and (2) found that a composition, using PHSRN (SEQ ID NO: 1) or a salt thereof that is allowable as a medical drug, is available as either or both of a preventive agent and treatment agent for corneal ulcer, corneal epithelial erosion, keratitis, dry eye, and other corneal disorder wherein the cornea is in a damaged state and have thereby come to basically complete the present invention.

This invention thus provides a new opthalmological composition that exhibits strong treatment effects against corneal disorder at small amounts, is low in molecular weight, and excellent in terms of safety.

More specifically, the present invention provides the following:

(1) An opthalmological composition, containing, as an effective component, the peptide, PHSRN (SEQ ID NO: 1), or a salt of this peptide that is allowable as a medical drug.

(2) Either or both of a corneal disorder preventive agent and a corneal disorder treatment agent, having, as an effective component, the peptide, PHSRN (SEQ ID NO: 1), or a salt of this peptide that is allowable as a medical drug.

(3) Either or both of the corneal disorder preventive agent and the corneal disorder treatment agent according to (2), with which the corneal disorder is corneal ulcer, corneal epithelial erosion, keratitis, or dry eye.

(4) Either or both of the corneal disorder preventive agent and the corneal disorder treatment agent according to (3), wherein the dosage form is an ophthalmic formulation.

(5) A corneal epithelium migration promoting agent having, as an effective component, the peptide, PHSRN (SEQ ID NO: 1), or a salt of this peptide that is allowable as a medical drug.

(6) The corneal epithelium migration promoting agent according to (5), wherein the dosage form is an ophthalmic formulation.

(7) Usage of an effective amount of the peptide, PHSRN (SEQ ID NO: 1), or a salt of this peptide that is allowable as a medical drug and a corneal disorder treatment method based on such usage.

In the present Specification, the following abbreviations shall be used for amino acid residues. That is Asn or N shall indicate asparagine, Arg or R shall indicate arginine, His or H shall indicate histidine, Pro or P shall indicate proline, and Ser or S shall indicate serine. Also, Ac shall indicate the acetyl group and $NH_2$ shall indicate the amino group.

The peptide, PHSRN (SEQ ID NO: 1), is the pentapeptide that is the active site of fibronectin and has the structure, Pro-His-Ser-Arg-Asn (SEQ ID NO: 1). In the case where these amino acids can generate a number of enantiomers, all such enantiomers and mixtures thereof are included within this invention. Compositions formed with the peptide, PHSRN (SEQ ID NO: 1), as a motif should be interpreted as being within the scope of equivalents and thus being within the scope of the claims of this invention. Also, a substance, with which the N terminal of the peptide, PHSRN (SEQ ID NO: 1), is acetylated and the C terminal is amidated, that is, Ac-Pro-His-Ser-Arg-Asn-$NH_2$ is preferable.

With the present invention, either or both of prevention and treatment refers to either or both of the prevention of the occurrence of a disease in advance (prevention) and the curing of a patient affected by a disease (therapeutics) by administration to an animal, including a human being.

With this invention, corneal disorder refers to corneal ulcer, corneal epithelial erosion, keratitis, dry eye, etc., wherein the cornea is in a damaged state due to any of various causes.

Examples of the salts of the peptide, PHSRN (SEQ ID NO: 1), that are allowable as a medical drug include chlorides, sulfates, phosphates, lactates, maleates, fumarates, oxalates, methanesulfonates, paratoluenesulfonates, etc.

The peptide, PHSRN (SEQ ID NO: 1), or a salt of this peptide that is allowable as a medical drug may be administered orally or non-orally. Dosage forms include pills, capsules, granules, powders, injectable solutions, ophthalmic formulations, etc. Among these, an ophthalmic formulation, such as an eye drop, eye ointment, etc., is preferable. These can be prepared by generally-used arts. For example, in the case of pills, capsules, granules, powders, and other oral agents, an excipient, such as lactose, crystalline cellulose, starch, or vegetable oil, a lubricant, such as magnesium stearate or talc, a binder, such as hydroxypropylcellulose or polyvinylpyrrolidone, a disintegrator, such as carboxymethylcellulose calcium or lowly-substituted hydroxypropylmethylcellulose, a coating agent, such as hydroxypropylmethylcellulose, macrogol, or silicon resin, a film-forming agent, such as a gelatin membrane, etc., may be added as necessary. An eye drop may be prepared using a tonicity agent, such as sodium chloride, a buffer agent, such as sodium phosphate, a preservative, such as benzalkonium chloride, etc. Though it is sufficient that the pH of such a medical drug be within a range allowable for an opthalmological formulation, the pH is preferably within the range of 4 to 8. An eye ointment may be prepared using a generally-used base material, such as white petrolatum or liquid paraffin.

This invention's corneal disorder treatment agent is preferably administered topically and especially preferably administered as an ophthalmic formulation. Though the concentration of the peptide, PHSRN (SEQ ID NO: 1), in the ophthalmic formulation may be set in accordance with the symptoms, age, etc., and is not restricted in particular, it is preferably in the range of 0.00001% to 1%. In the case of an eye drop, one to several drops at a time is administered once to several times a day. Besides a normal eye drop, the ophthalmic formulation may take on the form of a dissolve-on-use type eye drop or an eye ointment. For formulation, known arts may be employed, that is, an ophthalmic formulation may be prepared using a normally-used method and adding a tonicity agent, such as sodium chloride or potassium chloride, a buffer agent, such as sodium hydrogen phosphate, or sodium dihydrogen phosphate, a stabilizer, such as edetate sodium, a preservative, such as ethylparaben, butylparaben, or benzalkonium chloride, a pH adjuster, such as sodium hydroxide or dilute hydrochloric acid, an eye ointment base, such as white petrolatum or liquid paraffin, and other additives as necessary.

The peptide, PHSRN (SEQ ID NO: 1), of this invention can be produced simply and inexpensively by a solid phase method of growing the peptide chain from the C terminal on a insoluble polymer carrier, a liquid phase method that does not use a carrier, or other method that is normally used for peptide synthesis.

The use of the peptide, PHSRN (SEQ ID NO: 1), of this invention for commercially producing this invention's opthalmological preparation and treatment methods of using and administering the peptide, PHSRN (SEQ ID NO: 1), to a patient are also included within the scope of this invention.

BRIEF DESCRIPTION OF THE DRAWING (S)

FIG. 1 is a graph showing the effects of the peptide, PHSRN (SEQ ID NO: 1), on the migration of corneal epithelial cells. The abscissa indicates the concentration of the peptide, PHSRN (SEQ ID NO: 1) (0 (control), 51.2 nM, 102.5 nM, 153.7 nM, 256.2 nM, and 512.3 nM) and the ordinate indicates the migration length (μm) of the corneal epithelium.

DETAILED DESCRIPTION OF THE INVENTION

In order to examine the availability of the peptide, PHSRN (SEQ ID NO: 1), the present inventors examined the effects of the peptide, PHSRN (SEQ ID NO: 1), on corneal disorder. The details are indicated in the subsequent section on pharmacological tests. The present inventors have found that ophthalmic instillation of the peptide, PHSRN (SEQ ID NO: 1), provides (1) a corneal epithelium migration effect in a corneal organ culture system and (2) an effect of promoting wound healing after corneal epithelial abrasion. It has thereby become clear that the peptide, PHSRN (SEQ ID NO: 1), is available for the treatment of corneal disorder (that is, corneal ulcer, corneal epithelial erosion, keratitis, dry eye, and other disorder wherein the cornea is damaged due to various causes and especially corneal epithelial erosion) and dry eye.

Though preparation examples of this invention and the results of pharmacological tests shall now be described, the scope of the art of this invention is not limited to the embodiments described below and various modifications are possible without changing the gist of the invention. The scope of the art of this invention covers the scope of equivalents.

1. Preparation Examples

1) Eye Drops

As Formulation 1, an eye drop, containing 0.01 g of Ac-Pro-His-Ser-Arg-Asn-NH$_2$, 0.9 g of sodium chloride, and a suitable amount of sterilized purified water in a total amount of 100 ml, was prepared. In the same manner as Formulation 1, eye drops, respectively containing 0.00001 g, 0.00003 g, 0.0001 g, 0.0005 g, 0.001 g, 0.005 g, 0.05 g, and 0.1 g of Ac-Pro-His-Ser-Arg-Asn-NH$_2$ in a total amount of 100 ml, were prepared.

As Formulation 2, an eye drop, containing 0.1 g of Ac-Pro-His-Ser-Arg-Asn-NH$_2$, 0.8 g of sodium chloride, 0.1 g of sodium hydrogen phosphate, a suitable amount of sodium dihydrogen phosphate, and a suitable amount of sterilized purified water in a total amount of 100 ml, was prepared. In the same manner as Formulation 2, eye drops, respectively containing 0.00001 g, 0.00003 g, 0.0001 g, 0.0005 g, 0.001 g, 0.005 g, 0.05 g, and 0.1 g of Ac-Pro-His-Ser-Arg-Asn-NH$_2$ in a total amount of 100 ml, were prepared.

2) Eye Ointment

As Formulation 3, an eye ointment, containing 0.05 g of Ac-Pro-His-Ser-Arg-Asn-NH$_2$, 90 g of white petrolatum, and a suitable amount of liquid paraffin in a total amount of 100 g, was prepared. In the same manner as Formulation 3, eye ointments, respectively containing 0.00001 g, 0.00003 g, 0.0001 g, 0.0005 g, 0.001 g, 0.005 g, 0.05 g, and 0.1 g of Ac-Pro-His-Ser-Arg-Asn-NH$_2$ in a total amount of 100 g, were prepared.

2. Examples

Ac-Pro-His-Ser-Arg-Asn-NH$_2$ was synthesized by a solid phase method. Using this compound, (1) the in vitro corneal epithelium migrating action and (2) in vivo corneal wound healing promotion action were examined. The detailed data are indicated in the section on pharmacological tests.

In comparison to the control groups, migration of corneal epithelial cell layers and quick healing of corneal wounds were exhibited clearly by the groups to which Ac-Pro-His-Ser-Arg-Asn-NH$_2$ was added. It was thus proved that Ac-Pro-His-Ser-Arg-Asn-NH$_2$ is effective as a treatment agent for corneal disorder.

3. Pharmacological Tests (1) Action on Corneal Epithelium Migration (In Vitro)

Using the cornea of male Japanese white rabbits, the effects on corneal epithelium migration were examined using the migrating length of the corneal epithelium in a corneal organ culture system as an index in accordance with the method of Nishida et al. (J. Cell. Biol., 97, pp. 1653-1657 (1983)).

(Experimental Method)

Corneal blocks (three per group) were cutout from rabbit corneal tissue. These corneal blocks were incubated for 20 hours under the conditions of 37° C. and 5% $CO_2$ in a culture medium (Medium-199) containing the test compound. After incubation, the corneal blocks were fixed in a mixed solution of ethanol and glacial acetic acid (volume ratio of 95:5), embedded in paraffin, and prepared as sections. After deparaffination, the sections were stained with hematoxylin-eosin and the migrating length of the epithelial cell layer was measured under a microscope. As a control, corneal blocks incubated in a culture medium that does not contain the test compound was used.

(Results)

As shown in FIG. 1, incubation in a medium containing Ac-Pro-His-Ser-Arg-Asn-NH$_2$ exhibited significant promotion of the migration of corneal epithelium.

(2) Corneal Wound Healing Promotion Action 1 (In Vivo)

Using a male Japanese white rabbit, a wound of approximately 6 mm in diameter was produced in the cornea by inducing corneal epithelial abrasion in accordance with the method of Cintron et al. (Ophthalmic Res., 11, pp. 90-96 (1979)). The wound area was measured using the fluorescein-stained area as an index. The effects of the test compound on corneal wound healing were examined.

(Experimental Method)

The eye drops containing the respective concentrations of the test compound were instilled (30 μl at a time) at 0, 3, 6, 9, 12, 18, 24, 27, 30, 33, 36, 42, and 48 hours after inducing corneal epithelial abrasion. In measuring the wound area, fluorescein staining was carried out and a photograph of the cornea was measured. The fluorescein-stained area of the photographed cornea was computed using an image analysis processing system. As a control, a rabbit instilled with the base agent (PBS) that does not contain the test compound was used.

(Results)

Tables 1 and 2 below show the post-treatment effects of Ac-Pro-His-Ser-Arg-Asn-NH$_2$ (PHSRN (SEQ ID NO: 1)) on a rabbit corneal wound model in the form of healing ratio. As shown in Tables 1 and 2, the instillation of the peptide, PHSRN (SEQ ID NO: 1), exhibited significant promotion of wound healing.

In Tables 1 and 2, the respective values indicate the mean value±standard deviation (n=6). Statistical analysis was carried out using Dunnett's multiple comparison with respect to PBS with the area of the corneal wound portion immediately after (0 hours after) corneal epithelial abrasion being set to 100% (*$p<0.05$, **$p<0.01$; vs. control).

TABLE 1

<Post-treatment effects (healing ratio) of PHSRN (SEQ ID NO: 1) on a rabbit corneal wound model>

| Healing ratio (%) | 0 hr | 6 hr | 12 hr | 24 hr |
| --- | --- | --- | --- | --- |
| PBS | 0 | 4.96 ± 3.28 | 19.14 ± 5.04 | 54.36 ± 9.00 |
| 2 μM PHSRN (SEQ ID NO: 1) | 0 | 9.66 ± 2.21* | 26.71 ± 2.62** | 61.91 ± 3.08 |
| 20 μM PHSRN (SEQ ID NO: 1) | 0 | 10.73 ± 3.21** | 28.01 ± 1.92** | 64.07 ± 3.98* |
| 200 μM PHSRN (SEQ ID NO: 1) | 0 | 11.06 ± 3.50** | 28.69 ± 4.10** | 67.70 ± 5.37** |
| 2000 μM PHSRN (SEQ ID NO: 1) | 0 | 11.15 ± 1.25** | 28.99 ± 2.65** | 69.49 ± 3.17** |
| 5 μM EGF | 0 | 14.49 ± 3.42** | 31.63 ± 1.29** | 70.78 ± 6.91** |

TABLE 2

<Post-treatment effects (healing ratio) of PHSRN (SEQ ID NO: 1) on a rabbit corneal wound model>

| Healing ratio (%) | 36 hr | 48 hr |
| --- | --- | --- |
| PBS | 84.49 ± 11.60 | 97.09 ± 5.98 |
| 2 μM PHSRN (SEQ ID NO: 1) | 88.08 ± 4.03 | 99.14 ± 1.90 |
| 20 μM PHSRN (SEQ ID NO: 1) | 89.09 ± 6.42 | 99.15 ± 1.52 |
| 200 μM PHSRN (SEQ ID NO: 1) | 94.97 ± 4.63* | 100.00 ± 0.00 |
| 2000 μM PHSRN (SEQ ID NO: 1) | 95.39 ± 3.06* | 100.00 ± 0.00 |
| 5 μM EGF | 96.41 ± 3.97* | 99.58 ± 1.03 |

(3) Corneal Wound Healing Promotion Action 2 (In vivo)

Using the same method as (2) above, corneal epithelial abrasion was induced in a Japanese white rabbit to produce a wound of approximately 8 mm in diameter in the cornea. The wound area was measured using the fluorescein-stained area as an index to examine the effects on corneal wound healing.

(Experimental Method)

The eye drops containing the respective concentrations of the test compound were instilled (25 μl at a time) at 0, 6, 12, 18, 24, 30, 36, 42, 48, and 54 hours after induction corneal epithelial abrasion. In measuring the wound area, fluorescein staining was carried out and a photograph of the cornea was measured. The fluorescein-stained area of the photographed cornea was computed using an image analysis processing system. As a control, a rabbit instilled with the base agent (physiological saline) that does not contain the test compound was used.

(Results)

Tables 3 and 4 below show the post-treatment effects of Ac-Pro-His-Ser-Arg-Asn-NH$_2$ (PHSRN (SEQ ID NO: 1)) on a rabbit corneal wound model in the form of healing ratio. As shown in Tables 3 and 4, the instillation of the peptide, PHSRN (SEQ ID NO: 1), exhibited significant promotion of wound healing.

In Tables 3 and 4, the respective values indicate the mean value±standard deviation (n=6). Statistical analysis was carried out using Dunnett's multiple comparison with respect to physiological saline with the area of the corneal wound portion immediately after (0 hours after) corneal epithelial abrasion being set to 100% (*$p<0.05$, **$p<0.01$; vs. control).

TABLE 3

<Post-treatment effects (healing ratio) of PHSRN (SEQ ID NO: 1) on a rabbit corneal wound model>

| Healing ratio (%) | 0 hr | 12 hr | 18 hr | 24 hr | 30 hr |
| --- | --- | --- | --- | --- | --- |
| Physiological saline | 0 | 8.27 ± 3.38 | 23.12 ± 4.05 | 52.71 ± 5.36 | 52.71 ± 5.36 |
| 0.3% hyaluronic acid | 0 | 13.98 ± 4.88* | 28.45 ± 3.37* | 60.78 ± 8.07** | 60.78 ± 8.07* |
| 0.04% PHSRN (SEQ ID NO: 1) | 0 | 13.57 ± 3.74* | 29.45 ± 3.29** | 58.71 ± 6.32** | 58.71 ± 6.32** |

TABLE 4

<Post-treatment effects (healing ratio) of PHSRN (SEQ ID NO: 1) on a rabbit corneal wound model>

| Healing ratio (%) | 36 hr | 48 hr | 54 hr | 72 hr |
| --- | --- | --- | --- | --- |
| Physiological saline | 65.63 ± 6.69 | 87.06 ± 7.72 | 94.46 ± 6.50 | 99.72 ± 0.80 |
| 0.3% hyaluronic acid | 71.62 ± 11.02 | 90.19 ± 9.51 | 95.35 ± 6.44 | 99.92 ± 0.22 |
| 0.04% PHSRN (SEQ ID NO: 1) | 70.29 ± 8.38 | 88.27 ± 8.74 | 94.24 ± 6.62 | 98.93 ± 2.16 |

EFFECTS OF THE INVENTION

The above pharmacological tests show that the peptide, PHSRN (SEQ ID NO: 1), which is the minimum activity expression site of fibronectin, exhibits a wound healing promotion action on corneal epithelim and is available as either or both of a preventive agent and a treatment agent for corneal ulcer, corneal epithelial erosion, keratitis, dry eye, etc., wherein the cornea is subject to damage due to any of various causes.

The invention claimed is:

1. A method of treating a corneal epithelial disorder comprising topically administering a corneal epithelial disorder treating effective amount of an eye drop comprising the peptide PHSRN(SEQ ID NO: 1) or a pharmaceutically acceptable salt thereof, wherein the corneal epithelial disorder is selected from the group consisting of corneal ulcer and dry eye, and the peptide is present in a concentration of 0.0005 weight/volume % to about 1 weight/volume % in the eye drop.

2. The method of claim 1, wherein the eye drop comprising (i) the peptide PHSRN (SEQ ID NO: 1) or a pharmaceutically acceptable salt thereof further comprises (ii) a tonicity agent, (iii) a buffer agent and (iv) at least one member selected from the group consisting of a preservative, a stabilizer, and a pH adjuster.

3. The method of claim 1, wherein the eye drop comprising the peptide PHSRN (SEQ ID NO: 1) or a pharmaceutically acceptable salt thereof further comprises a base material.

4. A method of promoting the migration of corneal epithelial cells comprising topically administering to a subject in need thereof an effective amount of an eye drop comprising the peptide PHSRN (SEQ ID NO: 1) or a pharmaceutically acceptable salt thereof.

5. The method of claim 4, wherein the peptide is present in a concentration of 0.0005 weight/volume % to about 1 weight/volume % in the eye drop.

6. The method of claim 4, wherein the eye drop comprising (i) the peptide PHSRN (SEQ ID NO: 1) or a pharmaceutically acceptable salt thereof further comprises (ii) a tonicity agent, (iii) a buffer agent and (iv) at least one member selected from the group consisting of a preservative, a stabilizer, and a pH adjuster.

7. The method of claim 4, wherein the eye drop comprising the peptide PHSRN (SEQ ID NO: 1) or a pharmaceutically acceptable salt thereof further comprises a base material.

* * * * *